(12) United States Patent
O'Connor et al.

(10) Patent No.: US 8,507,230 B2
(45) Date of Patent: Aug. 13, 2013

(54) METHOD FOR PRODUCING POLYHYDROXYALKANOATE

(75) Inventors: Kevin O'Connor, Malahide (IE); Shane Kenny, Bray (IE); Jasmina Nikodinovic, Dublin (IE)

(73) Assignee: University College Dublin, National University of Ireland, Dublin (IE)

( * ) Notice: Subject to any disclaimer, the term of this patent is extended or adjusted under 35 U.S.C. 154(b) by 199 days.

(21) Appl. No.: 12/936,672

(22) PCT Filed: Apr. 6, 2009

(86) PCT No.: PCT/EP2009/054109
§ 371 (c)(1),
(2), (4) Date: Oct. 6, 2010

(87) PCT Pub. No.: WO2009/124918
PCT Pub. Date: Oct. 15, 2009

(65) Prior Publication Data
US 2011/0027843 A1 Feb. 3, 2011

(30) Foreign Application Priority Data

Apr. 7, 2008 (GB) ................................. 0806234.1
Jul. 30, 2008 (IE) ................................. S2008/0641

(51) Int. Cl.
*C12P 7/62* (2006.01)
*C12N 1/20* (2006.01)

(52) U.S. Cl.
USPC ........................................ 435/135; 435/253.3

(58) Field of Classification Search
None
See application file for complete search history.

(56) References Cited

U.S. PATENT DOCUMENTS 5,395,919 A 3/1995 Lee et al.
2011/0027843 A1 2/2011 O'Connor et al.

FOREIGN PATENT DOCUMENTS

| EP | 2276841 A2 | 1/2011 |
|---|---|---|
| WO | WO9218553 | 10/1992 |
| WO | 2009/124918 A2 | 10/2009 |

OTHER PUBLICATIONS

International Preliminary Report on Patentability in counterpart International Application No. PCT/EP2009/054109, dated Oct. 12, 2010, pp. 1-6.
Druckenlempler in counterpart European Application No. 09731052.8 dated Mar. 31, 2011, pp. 1-4.
Decision to grant in counterpart European Application No. 09731052.8 dated Aug. 11, 2011, pp. 1-2.
Yoshiaki, T., et al., "Pyrolysis of poly(ethylene terephthalate) in a fluidised bed plant," Polymer Degradation and Stability 86, Dec. 2004, vol. 86, No. 3, pp. 499-504, Elsevier Ltd.
Ward, Patrick G., et al., "Accumulation of Poyhydroxyalkanoate from Styrene and Phenylacetic Acid by Pseudomonas putida CA-3", Applied and Environmental Microbiology, Apr. 2005, vol. 71, No. 4, pp. 2046-2052.
Kenny, Shane T., et al., Up-Cycing of PET (Polyethylene Terephthalate) to Biodegradable Plastic PHA (Polyhydroxyalkanoate), Environ. Sci, Technol. Oct. 2008, vol. 42, No. 20, pp. 7696-7701.
PCT International Search Report.
PCT Written Opinion of the International Searching Authority.

*Primary Examiner* — Anand Desai
*Assistant Examiner* — Iqbal H Chowdhury
(74) *Attorney, Agent, or Firm* — Summa, Additon & Ashe, P.A.

(57) ABSTRACT

A method for producing polyhydroxyalkanoate (PHA), comprising (i) culturing in a culture medium comprising terephthalic acid and/or a salt thereof and/or an ester thereof one or more bacterial strains which are capable of accumulating PHA from terephthalic acid or a salt or ester thereof and which are selected from *Pseudomonas putida* strain GO16 having the accession number NCIMB 41538, *Pseudomonas putida* strain GO19 having the accession number NCIMB 41537, and *Pseudomonas frederiksbergensis* strain GO23 having the accession number NCIMB 41539; and (ii) recovering the PHA produced from the culture medium. The invention also provides *Pseudomonas putida* strain GO16 having the accession number NCIMB 41538; *Pseudomonas putida* strain GO19 having the accession number NCIMB 41537; and *Pseudomonas frederiksbergensis* strain GO23 having the accession number NCIMB 41539.

17 Claims, 3 Drawing Sheets

SEQUENCE LISTING

```
<160> NUMBER OF SEQ ID NOS: 11

<210> SEQ ID NO 1
<211> LENGTH: 1427
<212> TYPE: DNA
<213> ORGANISM: Pseudomonas putida GO16

<400> SEQUENCE: 1
gcggccgcgg gaattcgatt cgggcggtgt gtgtacaagg cccgggaacg tattcaccgc      60
gacattctga ttcgcgatta ctagcgattc cgacttcacg cagtcgagtt gcagactgcg     120
atccggacta cgatcggttt tatgggatta gctccacctc gcggcttggc aaccctctgt     180
accgaccatt gtagcacgtg tgtagcccag gccgtaaggg ccatgatgac ttgacgtcat     240
ccccaccttc ctccggtttg tcaccggcag tctccttaga gtgcccacca ttacgtgctg     300
gtaactaagg acaagggttg cgctcgttac gggacttaac ccaacatctc acgacacgag     360
ctgacgacag ccatgcagca cctgtctcaa tgttcccgaa ggcaccaatc catctctgga     420
aagttcattg gatgtcaagg cctggtaagg ttcttcgcgt tgcttcgaat taaaccacat     480
gctccaccgc ttgtgcgggc cccgtcaat tcatttgagt tttaaccttg cggccgtact     540
ccccaggcgg tcaacttaat gcgttagctg cgccactaag agctcaaggc tcccaacggc     600
tagttgacat cgtttacggc gtggactacc agggtatcta atcctgtttg ctccccacgc     660
tttcgcacct cagtgtcagt atcagtccag gtggtcgcct tcgccactgg tgttccttcc     720
tatatctacg catttcaccg ctacacagga aattccacca ccctctacca tactctagct     780
```

```
tgtcagtttt gaatgcagtt cccaggttga gcccggggct ttcacatcca acttaacaaa    840
ccacctacgc gcgctttacg cccagtaatt ccgattaacg cttgcaccct ctgtattacc    900
gcggctgctg gcacagagtt agccggtgct tattctgtcg gtaacgtcaa aacagcaaag    960
tattaattta ctgcccttcc tcccaactta aagtgcttta caatccgaag accttcttca   1020
cacacgcggc atggctggat caggctttcg cccattgtcc aatattcccc actgctgcct   1080
cccgtaggag tctggaccgt gtctcagttc cagtgtgact gatcatcctc tcagaccagt   1140
tacggatcgt cgccttggtg agccattacc tcaccaacta gctaatccga cctaggctca   1200
tctgatagcg caaggcccga aggtcccctg ctttctcccg taggacgtat gcggtattag   1260 cgtcccttc gagacgttgt cccccactac caggcagatt cctaggcatt actcacccgt    1320
ccgccgctga atcagagagc aagctctcat catccgctcg acttgcatgt gttaggcctg   1380
ccgccagcgt tcaatctgag ccaggatcaa actctaatca ctagtga                 1427

<210> SEQ ID NO 2
<211> LENGTH: 1401
<212> TYPE: DNA
<213> ORGANISM: Pseudomonas putida GO19

<400> SEQUENCE: 2
tagagtttga tcctggctca gattgaacgc tggcggcagg cctaacacat gcaagtcgag     60
cggatgatga gagcttgctc tctgattcag cggcggacgg gtgagtaatg cctaggaatc    120
tgcctggtag tgggggacaa cgtctcgaaa gggacgctaa taccgcatac gtcctacggg    180
agaaagcagg ggaccttcgg gccttgcgct atcagatgag cctaggtcgg attagctagt    240
tggtgaggta atggctcacc aaggcgacga tccgtaactg gtctgagagg atgatcagtc    300
acactggaac tgagacacgg tccagactcc tacgggaggc agcagtgggg aatattggac    360
aatgggcgaa agcctgatcc agccatgccg cgtgtgtgaa gaaggtcttc ggattgtaaa    420
gcactttaag ttgggaggaa gggcagtaaa ttaatacttt gctgttttga cgttaccgac    480
agaataagca ccggctaact ctgtgccagc agccgcggta atacagaggg tgcaagcgtt    540
aatcggaatt actgggcgta aagcgcgcgt aggtggtttg ttaagttgga tgtgaaatcc    600
ccgggctcaa cctgggaact gcattcaaaa ctgacaagct agagtatggt agagggtggt    660
ggaatttcct gtgtagcggt gaaatgcgta gatataggaa ggaacaccag tggcgaaggc    720
gaccacctgg actgatactg acactgaggt gcgaaagcgt ggtgggag caaacaggat    780 tagatacccct ggtagtccac gccgtaaacg atgtcaacta gccgttggga gccttgagct    840
cttagtggcg cagctaacgc attaagttga ccgcctgggg agtacggccg caaggttaaa    900
actcaaatga attgacgggg gcccgcacaa gcggtggagc atgtggttta attcgaagca    960
acgcgaagaa ccttaccagg ccttgacatc caatgaactt tccagagatg gattggtgcc   1020
ttcgggaaca ttgagacagg tgctgcatgg ctgtcgtcag ctcgtgtcgt gagatgttgg   1080
gttaagtccc gtaacgagcg caacccttgt ccttagttac cagcacgtaa tggtgggcac   1140
tctaaggaga ctgccggtga caaaccggag gaaggtgggg atgacgtcaa gtcatcatgg   1200
cccttacggc ctgggctaca cacgtgctac aatggtcggt acagagggtt gccaagccgc   1260
gaggtggagc taatcccata aaaccgatcg tagtccggat cgcagtctgc aactcgactg   1320
cgtgaagtcg gaatcgctag taatcgcgaa tcagaatgtc gcggtgaata cgttcccggg   1380
ccttgcacac acaccgcccg a                                             1401
```

```
<210> SEQ ID NO 3
<211> LENGTH: 1398
<212> TYPE: DNA
<213> ORGANISM: Pseudomonas frederiksbergensis GO23

<400> SEQUENCE: 3
cgattagagt ttgatcatgg ctcagattga acgctggcgg caggcctaac acatgcaagt      60
cgagcggcag cacgggtact tgtacctggt ggcgagcggc ggacgggtga gtaatgccta     120
ggaatctgcc tggtagtggg ggataacgct cggaaacgga cgctaatacc gcatacgtcc     180
tacgggagaa agcaggggac cttcgggcct tgcgctatca gatgagccta ggtcggatta     240
gctagttggt gaggtaatgg ctcaccaagg cgacgatccg taactggtct gagaggatga     300
tcagtcacac tggaactgag acacggtcca gactcctacg ggaggcagca gtggggaata     360
ttggacaatg ggcgaaagcc tgatccagcc atgccgcgtg tgtgaagaag gtcttcggat     420
tgtaaagcac tttaagttgg gaggaagggc atttacctaa tacgtaagtg ttttgacgtt     480
accgacagag taagcaccgg ctaactctgt gccagcagcc gcggtaatac agagggtgca     540
agcgttaatc ggaattactg ggcgtaaagc gcgcgtaggt ggttcgttaa gtcggatgtg     600
aaatccccgg gctcaacctg gaactgcatt caaaactgtc gagctagagt atggtagag      660 ggtggtggaa tttcctgtgt agcggtgaaa tgcgtagata taggaaggaa caccagtggc     720
gaaggcgacc acctggactg atactgacac tgaggtgcga aagcgtgggg agcaaacagg     780
attagatacc ctggtagtcc acgccgtaaa cgatgtcaac tagccgttgg gagccttgag     840
ctcttagtgg cgcagctaac gcattaagtt gaccgcctgg ggagtacggc cgcaaggtta     900
aaactcaaat gaattgacgg gggcccgcac aagcggtgga gcatgtggtt taattcgaag     960
caacgcgaag aaccttacca ggccttgaca tccaatgaac tttccagaga tggattggtg    1020
ccttcgggaa cattgagaca ggtgctgcat ggctgtcgtc agctcgtgtc gtgagatgtt    1080
gggttaagtc ccgtaacgag cgcaacccct gtccttagtt accagcacgt aatggtgggc    1140
actctaagga gactgccggt gacaaaccgg aggaaggtgg ggatgacgtc aagtcatcat    1200
ggcccttacg gcctgggcta cacacgtgct acaatggtcg gtacagaggg ttgccaagcc    1260
gcgaggtgga gctaatccca gaaaaccgat cgtagtccgg atcgcagtct gcaactcgac    1320
tgcgtgaagt cggaatcgct agtaatcgcg aatcagaatg tcgcggtgaa tacgttcccg    1380
ggccttgtac acaccg                                                   1398

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
agagtttgat cmtggctcag                                                 20

<210> SEQ ID NO 5
<211> LENGTH: 17
<212> TYPE: DNA
<213> ORGANISM: Artificial sequence
<220> FEATURE:
<223> OTHER INFORMATION: primer

<400> SEQUENCE: 5
acgggcggtg tgtgtrc                                                    17
```

<210> SEQ ID NO 6
<211> LENGTH: 1391
<212> TYPE: DNA
<213> ORGANISM: Pseudomonas putida GO13A

<400> SEQUENCE: 6

```
tagagtttga tcctggctca gattgaacgc tggcggcagg cctaacacat gcaagtcgag      60
cggatgatga gagcttgctc tctgattcag cggcggacgg gtgagtaatg cctaggaatc     120
tgcctggtag tgggggacaa cgtctcgaaa gggacgctaa taccgcatac gtcctacggg     180
agaaagcagg ggaccttcgg gccttgcgct atcagatgag cctaggtcgg attagctagt     240
tggtgaggta atggctcacc aaggcgacga tccgtaactg gtctgagagg atgatcagtc     300
acactggaac tgagacacgg tccagactcc tacgggaggc agcagtgggg aatattggac     360
aatgggcgaa agcctgatcc agccatgccg cgtgtgtgaa gaaggtcttc ggattgtaaa     420
gcactttaag ttgggaggaa gggcagtaaa ttaatacttt gctgttttga cgttaccgac     480
agaataagca ccggctaact ctgtgccagc agccgcggta atacagaggg tgcaagcgtt     540
aatcggaatt actgggcgta aagcgcgcgt aggtggtttg ttaagttgga tgtgaaagcc     600
ccgggctcaa cctgggaact gcattcaaaa ctgacaagct agagtatggt agagggtggt     660
ggaatttcct gtgtagcggt gaaatgcgta gatataggaa ggaacaccag tggcgaaggc     720
gaccacctgg actgatactg acactgaggt gcgaaagcgt ggggagcaaa caggattaga     780
taccctggta gtccacgccg taacgatgtc aactagccg ttgggagcct tgagctctta     840
gtggcgcagc taacgcatta agttgaccgc ctggggagta cggccgcaag gttaaaactc     900
aaatgaattg acgggggccc gcacaagcgg tggagcatgt ggtttaattc gaagcaacgc     960
gaagaacctt accaggcctt gacatccaat gaactttcca gagatggatt ggtgccttcg    1020
ggaacattga acaggtgct gcatggctgt cgtcagctcg tgtcgtgaga tgttgggtta    1080
agtcccgtaa cgagcgcaac ccttgtcctt agttaccagc acgtaatggt gggcactcta    1140
aggagactgc cggtgacaaa ccggaggaag gtggggatga cgtcaagtca tcatggccct    1200
tacggcctgg gctacacacg tgctacaatg gtcggtacag agggttgcca agccgcgagg    1260
tggagctaat cccataaaac cgatcgtagt ccggatcgca gtctgcaact cgactgcgtg    1320
aagtcggaat cgctagtaat cgcgaatcag aatgtcgcgg tgaatacgtt cccgggcctt    1380
gtacacacac c                                                         1391
```

<210> SEQ ID NO 7
<211> LENGTH: 1294
<212> TYPE: DNA
<213> ORGANISM: Pseudomonas putida GO 1

<400> SEQUENCE: 7

```
tgcagtcgag cggatgaaga gagcttgctc tctgattcag cggcggacgg gtgagtaatg     60
cctaggaatc tgcctggtag tgggggacaa cgtctcgaaa gggacgctaa taccgcatac    120
gtcctacggg agaaagcagg ggaccttcgg gccttgcgct atcagatgag cctaggtcgg    180
attagctagt tggtgaggta atggctcacc aaggcgacga tccgtaactg gtctgagagg    240
atgatcagtc acactggaac tgagacacgg tccagactcc tacgggaggc agcagtgggg    300
aatattggac aatgggcgaa agcctgatcc agccatgccg cgtgtgtgaa gaaggtcttc    360
ggattgtaaa gcactttaag ttgggaggaa gggcagtaaa ttaatacttt gctgttttga    420
cgttaccgac agaataagca ccggctaact ctgtgccagc agccgcggta atacagaggg    480
tgcaagcgtt aatcggaatt actgggcgta aagcgcgcgt aggtggtttg ttaagttgga    540
```

```
tgtgaaatcc ccgggctcaa cctgggaact gcattcaaaa ctgacaagct agagtatggt      600
agagggtggt ggaatttcct gtgtagcggt gaaatgcgta gatataggaa ggaacaccag      660
tggcgaaggc gaccacctgg actgatactg acactgaggt gcgaaagcgt ggggagcaaa      720
caggattaga taccctggta gtccacgccg taaacgatgt caactagccg ttgggagcct      780
tgagctctta gtggcgcagc taacgcatta agttgaccgc ctggggagta cggccgcaag      840
gttaaaactc aaatgaattg acgggggccc gcacaagcgg tggagcatgt ggtttaattc      900
gaagcaacgc gaagaacctt accaggcctt gacatccaat gaactttcca gagatggatt      960
ggtgccttcg ggacattga cacaggtgct gcatggctgt cgtcagctcg tgtcgtgaga     1020
tgttgggtta agtcccgtaa cgagcgcaac ccttgtcctt agttaccagc acgtaatggt     1080
gggcactcta aggagactgc cggtgacaaa ccggaggaag gtgggatga cgtcaagtca     1140 tcatggccct acggcctggg ctacacacg tgctacaatg gtcggtacag agggttgcca     1200
agccgcgagg tggagctaat cccataaaac cgatcgtagt ccggatcgca gtctgcaact     1260
cgactgcgtg aagtcggaat cgctagtaat cgcg                                 1294
```

```
<210> SEQ ID NO 8
<211> LENGTH: 1301
<212> TYPE: DNA
<213> ORGANISM: Pseudomonas putida GO 6
<220> FEATURE:
<221> NAME/KEY: misc_feature
<222> LOCATION: (52)..(54)
<223> OTHER INFORMATION: n is a, c, g, or t

<400> SEQUENCE: 8
```

```
tgcagtcgag cggatgaaga gagcttgctc tctgattcag cggcggacgg gnnnagtaat       60
gcctaggaat ctgcctggta gtgggggaca acgtctcgaa agggacgcta ataccgcata      120
cgtcctacgg gagaaagcag gggaccttcg ggccttgcgc tatcagatga gcctaggtcg      180
gattagctag ttggtgaggt aatggctcac caaggcgacg atccgtaact ggtctgagag      240
gatgatcagt cacactggaa ctgagacacg gtccagactc ctacgggagg cagcagtggg      300
gaatattgga caatgggcga aagcctgatc cagccatgcc gcgtgtgtga agaaggtctt      360
cggattgtaa agcactttaa gttgggagga agggcagtaa cttaatacgt tgctgttttg      420
acgttaccga cagaataagc accggctaac tctgtgccag cagccgcggt aatacagagg      480
gtgcaagcgt taatcggaat tactgggcgt aaagcgcgcg taggtggttt gttaagttgg      540
atgtgaaagc cccgggctca acctgggaac tgcattcaaa actgacaagc tagagtatgg      600
tagagggtgg tggaatttcc tgtgtagcgg tgaaatgcgt agatatagga aggaacacca      660
gtggcgaagg cgaccacctg gactgatact gacactgagg tgcgaaagcg tggggagcaa      720
acaggattag ataccctggt agtccacgcc gtaaacgatg tcaactagcc gttgggagcc      780
ttgagctctt agtggcgcag ctaacgcatt aagttgaccg cctggggagt acggccgcaa      840
ggttaaaact caaatgaatt gacggggggcc cgcacaagcg tggagcatg tggtttaatt      900 cgaagcaacg cgaagaacct taccaggcct tgacatccaa tgaactttcc agagatggat      960
tggtgccttc gggaacattg agacaggtgc tgcatggctg tcgtcagctc gtgtcgtgag     1020
atgttgggtt aagtcccgta acgagcgcaa cccttgtcct tagttaccag cacgtaatgg     1080
tgggcactct aaggagactg ccggtgacaa accggaggaa ggtggggatg acgtcaagtc     1140
atcatggccc ttacgcctg gctacacac gtgctacaat ggtcggtaca gagggttgcc     1200
aagccgcgag gtggagctaa tcccataaaa ccgatcgtag tccggatcgc agtctgcaac     1260
```
tcgactgcgt gaagtcggaa tcgctagtaa tcgcgaatca g        1301

<210> SEQ ID NO 9
<211> LENGTH: 1310
<212> TYPE: DNA
<213> ORGANISM: Pseudomonas sp. GO 8
<220> FEATURE:
<221> NAME/KEY: misc_feature
<222> LOCATION: (59)..(61)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t

<400> SEQUENCE: 9
ctacacatgc agtcgagcgg cagcacgggt acttgtacct ggtggcgagc ggcggacgnn        60
ngagtaatgc ctaggaatct gcctggtagt gggggataac gctcggaaac ggacgctaat       120
accgcatacg tcctacggga gaaagcaggg gaccttcggg ccttgcgcta tcagatgagc       180
ctaggtcgga ttagctagtt ggtgaggtaa tggctcacca aggcgacgat ccgtaactgg       240
tctgagagga tgatcagtca cactggaact gagacacggt ccagactant acggaggca       300 gcagtgggga atattggaca atgggcgaaa gcctgatcca gccatgccgc gtgtgtgaag       360
aaggtcttcg gattgtaaag cactttaagt tgggaggaag gcattaacc taatacgttg        420 gtgtcttgac gttaccgaca gaatnagcac cggctaantc tgtgccagca gccgcggtaa       480
tacagagggt gcaagcgtta atcggaatta ctgggcgtaa agcgcgcgta ggtggtttgt       540
taagttggat gtgaaatccc cgggctcaac ctgggaactg cattcaaaac tgacaagcta       600
gagtatggta gagggtggtg gaatttcctg tgtagcggtg aaatgcgtag atataggaag       660
gaacaccagt ggcgaaggcg accacctgga ctgatactga cactgaggtg cgaaagcgtg       720
gggagcaaac aggattagat accctggtag tccacgccgt aaacgatgtc aactagccgt       780
tgggagcctt gagctcttag tggcgcagct aacgcattaa gttgaccgcc tggggagtac       840
ggccgcaagg ttaaaactca aatgaattga cggggcccg cacaagcggt ggagcatgtg        900
gtttaattcg aagcaacgcg aagaacctta ccaggccttg acatccaatg aacttttccag      960 agatggattg gtgccttcgg gaacattgag acaggtgctg catggctgtc gtcagctcgt      1020
gtcgtgagat gttgggttaa gtcccgtaac gagcgcaacc cttgtcctta gttaccagca     1080
cgttatggtg ggcactctaa ggagactgcc ggtgacaaac cggaggaagg tggggatgac     1140
gtcaagtcat catggccctt acggcctggg ctacacacgt gctacaatgg tcggtacaga     1200
gggttgccaa gccgcgaggt ggagctaatc ccagaaaacc gatcgtagtc cggatcgcag     1260
tctgcaactc gactgcgtga agtcggaatc gctagtaatc gcgaatcaga                 1310

<210> SEQ ID NO 10
<211> LENGTH: 1393
<212> TYPE: DNA
<213> ORGANISM: Burkholderia glathei GO 14

<400> SEQUENCE: 10
tagagtttga tcatggctca gattgaacgc tggcggcatg ccttacacat gcaagtcgaa        60

```
cggcagcacg ggggcaaccc tggtggcgag tggcgaacgg gtgagtaata catcggaacg    120
tgtcctgtag tggggatag  cccggcgaaa gccggattaa taccgcatac gatctacgga    180
agaaagcggg ggatcttcgg acctcgcgct ataggggcgg ccgatggcag attagctagt    240 tggtgggta  aaggcctacc aaggcgacga tctgtagctg gtctgagagg acgaccagcc    300
acactgggac tgagacacgg cccagactcc tacgggaggc agcagtgggg aattttggac    360
aatgggggaa accctgatcc agcaatgccg cgtgtgtgaa gaaggccttc gggttgtaaa    420
gcacttttgt ccggaaagaa aacttcgggg ctaataccctc tggaggatga cggtaccgga    480
agaataagca ccggctaact acgtgccagc agccgcggta atacgtaggg tgcgagcgtt    540
aatcggaatt actgggcgta aagcgtgcgc aggcggtctg ttaagacaga tgtgaaatcc    600
ccgggcttaa cctgggaact gcatttgtga ctggcaggct agagtatggc agagggggt    660 agaattccac gtgtagcagt gaaatgcgta gagatgtgga ggaataccga tggcgaaggc    720
agccccctgg gccaatactg acgctcatgc acgaaagcgt ggggagcaaa caggattaga    780
taccctggta gtccacgccc taaacgatgt caactagttg ttgggattc  atttccttag    840 taacgtagct aacgcgtgaa gttgaccgcc tgggagtac  ggtcgcaaga ttaaaactca    900
aaggaattga cggggacccg cacaagcggt ggatgatgtg gattaattcg atgcaacgcg    960
aaaaacctta cctaccttg  acatggtcgg aaccctggtg agagctgggg gtgctcgaaa    1020
gagaaccgac acacaggtgc tgcatggctg tcgtcagctc gtgtcgtgag atgttgggtt    1080
aagtcccgca acgagcgcaa cccttgtcct tagttgctac gcaagagcac tctaaggaga    1140
ctgccggtga caaaccggag gaaggtgggg atgacgtcaa gtcctcatgg cccttatggg    1200
tagggcttca cacgtcatac aatggtcgga acagagggtc gctaagccgc gaggtggagc    1260
caatcccaga aaaccgatcg tagtccggat cgtagtctgc aactcgacta cgtgaagctg    1320
gaatcgctag taatcgcgga tcagcatgcc gcggtgaata cgttcccggg tcttgtacac    1380
acaccgcccg taa                                                      1393
```

<210> SEQ ID NO 11
<211> LENGTH: 1520
<212> TYPE: DNA
<213> ORGANISM: Stenotrophomonas sp. TA 1

<400> SEQUENCE: 11

```
gcccgacgtc gcatgctccc ggccgccatg gcggccgcgg gaattcgatt agagtttgat     60
cctggctcag agtgaacgct ggcggtaggc ctaacacatg caagtcgaac ggcagcacag    120
gagagcttgc tctctgggtg gcgagtggcg gacgggtgag gaatacatcg gaatctactt    180
tttcgtgggg gataacgtag ggaaacttac gctaataccg catacgacct acgggtgaaa    240 gcagggggatc ttcggacctt gcgcgattga atgagccgat gtcggattag ctagttggcg    300
gggtaaaggc ccaccaaggc gacgatccgt agctggtctg agaggatgat cagccacact    360
ggaactgaga cacggtccag actcctacgg gaggcagcag tggggaatat tggacaatgg    420
gcgcaagcct gatccagcca taccgcgtgg gtgaagaagg ccttcgggtt gtaaagccct    480
tttgttggga aagaaatcca gctggctaat accggttgg  gatgacggta cccaaagaat    540
aagcaccggc taacttcgtg ccagcagccg cggtaatacg aagggtgcaa gcgttactcg    600
gaattactgg gcgtaaagcg tgcgtaggtg gtcgtttaag tccgttgtga aagccctggg    660
ctcaacctgg gaactgcagt ggatactggg cgactagagt gtggtagagg gtagcggaat    720
tcctggtgta gcagtgaaat gcgtagagat caggaggaac atccatggcg aaggcagcta    780
```

```
cctggaccaa cactgacact gaggcacgaa agcgtgggga gcaaacagga ttagataccc      840
tggtagtcca cgccctaaac gatgcgaact ggatgttggg tgcaatttgg cacgcagtat      900
cgaagctaac gcgttaagtt cgccgcctgg ggagtacggt cgcaagactg aaactcaaag      960
gaattgacgg gggcccgcac aagcggtgga gtatgtggtt taattcgatg caacgcgaag     1020
aaccttacct ggccttgaca tgtcgagaac tttccagaga tggattggtg ccttcgggga     1080
ctcgaacaca ggtgctgcat ggctgtcgtc agctcgtgtc gtgagatgtt gggttaagtc     1140
ccgcaacgag cgcaaccctt gtccttagtt gccagcacgt aatggtggga actctaagga     1200
gaccgccggt gacaaaccgg aggaaggtgg ggatgacgtc aagtcatcat ggcccttacg     1260
gccagggcta cacacgtact acaatggtag ggacagaggg ctgcaagccg gcgacggtaa     1320
gccaatccca gaaaccctat ctcagtccgg attggagtct gcaactcgac tccatgaagt     1380
cggaatcgct agtaatcgca gatcagcatt gctgcggtga atacgttccc gggccttgca     1440
ccaccgcccg taatcactag tgaattcgcg gccgcctgca ggtcgaccat atgggagagc     1500
tcccaacgcg tggatgcata                                                 1520
```

METHOD FOR PRODUCING POLYHYDROXYALKANOATE

CROSS-REFERENCE TO RELATED APPLICATIONS

This application is a national stage application under 35 U.S.C. 371 of International Application No. PCT/EP2009/054109 filed 6 Apr. 2009, which claims priority to United Kingdom Application No. GB 0806234.1 filed 7 Apr. 2008, and Irish Application No. IE S2008/0641 filed 30 Jul. 2008, the disclosures of which are expressly incorporated herein by reference.

The present invention relates to a method for producing polyhydroxyalkanoate (PHA) and to novel bacterial strains used in the method.

Polyethylene terephthalate (PET) is one of many petrochemical based plastics that contribute greatly to the convenience of everyday life. Best known worldwide for its use in plastic bottles, it is produced on a multi-million tonne scale worldwide. Due to the success of PET it has, like other plastics, become a major waste problem. Greater than 5,400 million lbs (2,400 million kg) of PET bottles were on shelves in the United States in 2006. In general, less than 25% of these bottles are recycled, and thus the vast majority of PET bottles worldwide end up in landfill. This occurs despite a variety of recycling technologies being available such as mechanical grinding for use of waste PET in the fiber industry, reprocessing of waste PET for food contact usage, and pyrolysis (thermal treatment in the absence of air) of waste PET to generate chemical feedstocks.

PET can be degraded by pyrolysis to its monomeric components, terephthalic acid and ethylene glycol. However, the resulting terephthalic acid is generally used as a chemical feedstock for the re-synthesis of PET, which is a non-biodegradable and consequently low value product. Thus, factors such as the high relative cost of sorting of waste PET and the low value of the downstream product, contribute to the poor recycling rates for PET.

PHA is the general term for a range of diverse biodegradable polymers that consist of polyesters of (R)-3-hydroxyalkanoic acids. These polymers are of interest due to a broad range of applications and the fact that they are completely biodegradable thus offering little or no long teim waste issues.

These polymers can be accumulated by some bacteria intracellularly as carbon storage materials. It has been shown that PHA accumulation occurs in bacteria in response to a range of environmental stress factors such as inorganic nutrient limitation. The substrates that are supplied to bacteria to accumulate PHA are divided into two groups 1) PHA related substrates, i.e. alkanoic acids (fatty acids) that resemble the monomers that make up PHA ((R)-3-hydroxyalkanoic acids) and 2) PHA unrelated substrates, which are substrates that do not resemble the monomers that make up PHA e.g. glucose.

It is an object of the invention to mitigate or eliminate the disadvantages associated with the recycling of PET.

It is also an object of the invention to provide a method for producing PHA from the degradation product of PET, namely terephthalic acid and/or a salt thereof and/or an ester thereof.

According to the invention, there is provided a method for producing polyhydroxyalkanoate (PHA), comprising (i) culturing in a culture medium comprising terephthalic acid and/or a salt thereof and/or an ester thereof one or more bacterial strains which are capable of accumulating PHA from terephthalic acid or a salt or ester thereof and which are selected from *Pseudomonas putida* strain GO16 having the accession number NCIMB 41538, *Pseudomonas putida* strain GO19 having the accession number NCIMB 41537, and *Pseudomonas frederiksbergensis* strain GO23 having the accession number NCIMB 41539; and (ii) recovering the PHA produced from the culture medium.

The invention also provides *Pseudomonas putida* strain GO16 having the accession number NCIMB 41538. The 16S rDNA sequence of strain GO16, presented in SEQ ID NO. 1, shares 99% homology with a known *Pseudomonas putida* strain (DQ133506, see Table 2).

The invention further provides *Pseudomonas putida* strain GO19 having the accession number NCIMB 41537. The 16S rDNA sequence of strain GO19, presented in SEQ ID NO. 2, shares 99% homology with a known *Pseudomonas putida* strain (AY512611, see Table 2).

The invention still further provides *Pseudomonas frederiksbergensis* strain GO23 having the accession number NCIMB 41539. The 16S rDNA sequence of strain GO23, presented in SEQ ID NO. 3, shares 99% homology with a known *Pseudomonas frederiksbergensis* strain (AJ249382, see Table 2).

Each of the strains *Pseudomonas putida* GO16, *Pseudomonas putida* strain GO 19 and *Pseudomonas frederiksbergensis* strain GO23 is capable of accumulating PHA from terephthalic acid or a salt or ester thereof.

As described in more detail in Example 1 (A) below, the base sequence of 16S rDNA of each of the strains of the invention was analysed and identified using the NCBI GenBank database BLAST programme (http://blast.nebi.nlm.nih.gov/Blast.cgi), and each of the strains was deposited on Jan. 24, 2008 in the depositary institution NCIMB Ltd, Ferguson Building, Craibstone Estate, Bucksburn, Aberdeen AB21 9YA, Scotland, an International Depository Authority under the Budapest Treaty.

The PHA recovered from the culture medium advantageously comprises at least 80%, preferably at least 85%, more preferably at least 90%, most preferably at least 95% medium chain length (mcl) PHA. MclPHA is classified as comprising repeating units derived from 3-hydroxyalkanoic acid monomers containing 6 carbon atoms (C6) to 14 carbon atoms (C14). Preferably, at least 80%, more preferably 85%, even more preferably at least 90%, most preferably at least 95% of the mclPHA comprises repeating units of C8, C10 and C12 monomers. More preferably, the mclPHA comprises repeating units in a respective amount by weight of mclPHA of 15%-25% C8, 40%-50% C10 and 30%-40% C12, preferably as determined using an Agilent 6890N series gas chromatograph (GC) fitted with a 30 m×0.25 mm×0.25 μm BP-21 column (J & W Scientific), and further preferably as confirmed using an Agilent 6890N GC fitted with a 5973 series inert mass spectrophotometer, using a 12 m×0.2 mm×0.33 μm HP-1 column (Hewlett-Packard). In a preferred embodiment, the amount of C8, C10 and C12 totals 100%.

PHAs are generally classified as short chain length PHAs (sclPHAs), medium chain length PHAs (mclPHAs) or long chain length PHAs (lclPHAs), depending upon the number of carbon atoms of the constituting monomers thereof. SclPHA comprises monomers of C3-C5, mclPHA comprises monomers of C6-C14, and lclPHA comprises monomers of more than 14 carbons (>C14). This variation in monomer chain length gives rise to different properties in the polymer, with sclPHAs and lclPHAs both having undesirable properties, sclPHAs having a high degree of crystallinity and being rigid and brittle, and lclPHAs being sticky and very difficult to handle. The properties of sclPHAs and lclPHAs limit the range of their applications. McIPHAs, as produced by the method of the invention, and which may comprise monomers selected from C6, C8, C10, C12 and C14 monomers, have much more desirable properties, being elastomers with a low glass transition temperature and having properties being suitable to a wide range of applications including biodegradable rubber and coating materials. Therefore, the production of mclPHA according to the invention advantageously provides a polymer which has a wide range of applications and is biodegradable.

Salts of terephthalic acid useful in the invention include alkali metal and alkaline earth metal salts and mixtures thereof, such as sodium and potassium salts, and magnesium, calcium and barium salts. Mono- or di-sodium or potassium salts of terephthalic acid are preferred. Monosodium terephthalate is especially preferred. In an especially preferred embodiment, the terephthalic acid or salt or ester thereof is in the form of monosodium terephthalate, also referred to herein as sodium terephthalate or terephthalic acid (sodium salt).

Esters of terephthalic acid which can be used in the invention include mono- and di-esters of terephthalic acid and mixtures thereof. Suitable mono- and di-esters of terephthalic acid include mono- and di-C1-C4 alkyl esters and mono- and di-glycol esters.

The terephthalic acid or salt or ester thereof may be obtained from hydrolysis or pyrolysis of polyethylene terephthalate (PET), preferably pyrolysis of PET, which produces a solid, liquid and gaseous fraction. If a terephthalate salt is required, the solid fraction is reacted with a base, preferably with an alkali metal or alkaline earth metal hydroxide. If an ester is required, the solid fraction is reacted with a suitable alcohol. In a particularly preferred embodiment, the solid fraction obtained by pyrolysis of PET is reacted with sodium hydroxide, to form sodium terephthalate.

The method of the invention preferably comprises culturing the one or more strains in the culture medium for a period of from about 12 hours to about 72 hours, more preferably from about 24 hours to about 60 hours, most preferably about 48 hours, at a temperature of from about 25° C. to about 35° C., preferably about 30° C.

In the method of the invention, the culture medium preferably comprises strain GO19 and/or strain GO16.

In the method of the invention, the culture medium is preferably nitrogen limited, with a maximum nitrogen content of about 0.5 g/l, preferably 0.067 g/l culture medium. A suitable nitrogen source is sodium ammonium phosphate ($NaNH_4HPO_4.4H_2O$).

In the method of the invention, recovering the PHA produced from the culture medium preferably comprises extracting the PHA produced using the following method. The cultures are harvested by centrifugation at 6000×g/20 min, cells collected and resuspended in $\frac{1}{100}$ of the original culture volume of 50 mM phosphate buffer (pH 7). Cell suspensions are centrifuged again at 6000×g/20 min and supernatant discarded. Cell pellets are freeze dried. Dry cell material is resuspended in 10 volumes of acetone and the suspension is stirred vigorously at 25° C. for 12-20 h. Suspension is then centrifuged at 6000 rpm×g/20 min and the supernatant retained. Supernatant is filtered through 1 μm PTFE filter and the solvent evaporated in vacuo to $\frac{1}{10}$-$\frac{1}{25}$ of the original volume. The product is a PHA suspension that is then dropwise added to chilled methanol (in the ratio 1:20). PHA polymer is harvested by centrifugation at 6000 rpm×g/20 min and dried under vacuum.

Advantages of the invention include the following:
It provides a clean, low cost method for producing PHA.
The cost of PHA production through fermentation is inextricably linked to the cost of the starting substrate. Thus, the use of terephthalic acid (sodium salt), the degradation product of an easily sourced and inexpensive petrochemical waste plastic (PET), as a feedstock for bacteria as described herein, provides a cheap, clean and reliable source for the synthesis of PHA.

The PHA produced is a high value polymer. Specifically, in contrast to sclPHAs having a high degree of crystallinity and being rigid and brittle, and lclPHAs being sticky and very difficult to handle, the PHAs capable of being produced herein are mclPHAs having much more desirable properties, being elastomers with a low glass transition temperature.

The PHA produced is completely biodegradable and has a wide range of applications ranging from biomedical applications to packaging.

The following examples serve to illustrate the invention but it will be appreciated that the invention is not limited to these examples:

Example 1 (A)

Hydrolytic Pyrolysis of PET

Virgin polyethylene terephthalate (PET) (Krupp-Formoplast) was supplied to a laboratory scale pyrolysis plant (as described in Yoshioka et al, 2004. Pyrolysis of poly(ethylene terephthalate) in a fluidized bed plant. Polymer Degradation and Stability. 86:499-504) at a feed rate of 1,035 kg/h. The electrically heated fluidized bed had a diameter of 130 mm. 9 kg quartz sand with diameters between 0.3 and 0.5 mm led to a height of 480 mm in the fluidized bed which was maintained at a temperature of 450° C. The PET entered the fluidized bed reactor via a screw conveyor. The hot pyrolysis products (see Table 1) passed a cyclone to be cleaned by small amounts of fillers and then were cooled down by mixing with cold water to room temperature in a precipitator (desublimator). In the precipitator, the whole solid fraction including the terephthalic acid was desublimated to generate a white powder. The sand bed was fluidized by steam with a flow rate of 2.5 kg/h. The solids were analyzed by HPLC-MS-system (HP 1100, column Multospher® 100) using a diode array detector by 220 nm. The gas and oil fractions were characterized by gas chromatography (GC-FID, HP 5890 Machery & Nagel SE 52) and GC-MS (Fisons Instruments VG 70 SE, Machery & Nagel SE 52).

Bacterial Growth Medium

The minimal medium E2 (per litre: 3.5 g $NaNH_4HPO_4.4H_2O$, 7.5 g $K_2HPO_4.3H_2O$, 3.7 g $KH_2PO_4$, 0.25 g $MgSO_4.7H_2O$, 2.78 g $FeSO_4.7H_2O$, 1.98 g $MnCl_2.4H_2O$, 2.81 g $CoSO_4.7H_2O$, 1.47 g $CaCl_2.2H_2O$, 0.17 g $CuCl_2.2H_2O$, 0.29 g $ZnSO_4.7H_2O$; for limited nitrogen conditions, 1.0 g/l of $NaNH_4HPO_4.4H_2O$ was used) was prepared, and used as the base media supplemented with sodium terephthalate as the sole source of carbon and energy for all culture techniques discussed herein. The sodium terephthalate was prepared by taking the whole solid fraction of PET pyrolysis (in the form of the white powder mentioned above) and dissolving it in an equimolar solution of sodium hydroxide (Sigma).

Isolation of Bacteria from Soil 1 kg of soil was collected from PET exposed soil at an industrial site in Ireland used to mould PET granules to PET products. The granules were present in the soil adjacent to the factory setting. The soil was sieved under aseptic conditions to a particle size of 5 mm, then 10 g of soil were added to 90 ml of sterile Ringer's solution (Sigma), this was vortexed for 5 min to homogenize the sample. 1 ml of this was added to 9 ml of sterile Ringer's, this was repeated to obtain a $10^{-5}$ dilution of the original soil sample. The serial dilutions were spread plated on solid E2 media containing 1.1 g/l of sodium terephthalate as the sole source of carbon and energy. 32 isolates were selected by visual differentiation of contrasting colony morphology. These 32 isolates from the soil samples were then grown in shake flask culture as described below and tested for PHA accumulation.

Growth Conditions for PHA Accumulation

The 32 soil isolates were grown in shake flask experiments, where each strain was grown in a 250 ml Erlenmeyer flask containing 50 ml E2 medium (4.2 g TA/l) at 30° C. with shaking at 200 rpm. To screen for organisms capable of PHA accumulation, the inorganic nitrogen source sodium ammonium phosphate ($NaNH_4HPO_4.4H_2O$) was limited to 1 g/l (67 mg nitrogen/l).

PHA Screening and Composition Analysis.

The 32 soil isolates were grown in shake flasks as described above for 48 hours and tested for PHA accumulation as follows. Cell material (5-10 mg) or PHA standard isolated from *P. putida* CA-3 for which the PHA composition is known (Ward PG, de Roo G, O'Connor K E. Accumulation of polyhydroxyalkanoate from styrene and phenylacetic acid by *Pseudomonas putida* CA-3. Appl Environ Microbiol. 2005 April; 71(4):2046-52) was resuspended in 2 ml acidified methanol (15% $H_2SO_4$, v/v) and 2 ml of chloroform containing 6 mg/l benzoate methyl ester as an internal standard. The mixture was placed in 15 ml Pyrex test tubes and incubated at 100° C. for 3 h (with frequent inversions). The solution was extracted with 1 ml of water (vigorous vortex 2 min). The phases were allowed to separate before removing the top layer (water). The organic phase (bottom layer) was dried with $Na_2SO_4$ before further analysis. The samples were analyzed on an Agilent 6890N series gas chromatograph (GC) fitted with a 30 m×0.25 mm×0.25 μm BP-21 column (J & W Scientific) using a split mode (split ratio 10:1). An oven method was employed comprising 60° C. for 2 min, increasing by 5° C./min to 200° C. for 1 min. For peak identification, commercially obtained (R)-3-hydroxydodecanoic acids (Sigma) and the above-identified PHA standard (Ward et al., 2005) were used. PHA monomer determination was confirmed using an Agilent 6890N GC fitted with a 5973 series inert mass spectrophotometer, using a 12 m×0.2 mm×0.33 μm HP-1 column (Hewlett-Packard), with an oven method of 50° C. for 3 min, increasing by 10° C./min to 250° C. for 1 min and comparing to the above-mentioned standards. Only 3 strains exhibited high optical densities (OD540 of 4.0) and were found to produce PHA. These 3 strains were selected for further analysis, as discussed below. Additionally, 6 other strains exhibiting good growth (OD540 of 4.0) but which did not produce PHA, were randomly selected for comparison as described in more detail in Example 1 (B).

Nitrogen Determination Assay

The concentration of nitrogen in the growth media was monitored over time using the following method. The concentration of nitrogen (ammonium ion) in the media was monitored by taking 1 ml samples from the culture flask at various time points and centrifuging the samples at 13,200 rpm for 2 min. The supernatant was retained and diluted 100 fold in deionised water. 1 ml of phenol-nitropruside buffer (per liter: 30 g $Na_3PO_4.12H_2O$; 30 g $Na_3C_5H_5O_7$; 3 g EDTA, pH 12; 120 g phenol) was added to 2.5 ml of diluted sample and mixed. 1.5 ml of hypochloride solution (52.5 ml of sodium hypochloride solution (4% available chlorine) to 1000 ml of 1M NaOH) was added to the mixture and mixed by inversion. The colour was allowed to develop for 45 min at 25° C. in dark. The absorbance at 635 nm was read using Helios delta spectrophotomer. Standard curve was also generated using known concentrations of sodium ammonium phosphate.

Determination of Terephthalic Acid Utilization During Growth.

The concentration of TA in the media was monitored by taking 1 ml samples from the culture flask at various time points and centrifuging the samples at 13,200 rpm for 2 min. The supernatant was retained, filtered and analyzed by HPLC. In order to analyze the sample and maintain a linear relationship between peak area on the HPLC chromatograph and TA concentration, samples had to be diluted so that the concentration of TA in the final preparation did not exceed 0.63 g/l. A standard curve of TA concentrations from commercially obtained sodium terephthalate (Sigma) was generated to establish the relationship between TA concentration and peak area on the HPLC. An Agilent 1100 series HPLC using a C18 ODS Hypersil column (125 mm×3 mm, particle size 5 μm) (Thermo) was used and samples were isocratically eluted using 0.2% Formic acid and Acetonitrile (ratio 80:20 respectively) at 0.5 ml/min and read on a UV-Vis detector at 230 nm.

Determination of PHA Polymer Properties

Nuclear magnetic resonance (NMR).

Solution NMR were recorded on a Bruker DPX400 with $^1H$ at 400.13 MHz and $^{13}C$ at 100.62 MHz. The 400 MHz $^1H$ and $^{13}C$-NMR spectra of PHA isolated from *P. putida* GO19 recorded at 20° C. in $CDCl_3$ are shown in FIGS. 2 and 3 respectively. The solvent chloroform-d and tetramethylsilane (TMS) were used as internal references for chemical shifts in $^{13}C$ and $^1H$ NMR, respectively. $^{13}C$ NMR spectra were recorded with proton-decoupling. Typically 2200 transients were accumulated. Spectrometer peak areas were obtained directly by standard signal integration.

Thermal Analysis.

Differential Scanning calorimetry (DSC) was performed with Perkin Elmer Pyris-Diamond calorimeter calibrated to Indium standards. The samples weighing 7-8 mg were encapsulated in hermetically sealed aluminum pans and heated from −70° C. to 100° C. at a rate of 10° C./min. To determine the glass transition temperature (Tg), the samples were held at 100° C. for 1 min and rapidly quenched to −70° C. The samples were then re-heated from −70° C. to 100° C. at 10° C./min to determine the melting temperature (Tm) and Tg. The Tm was taken at the peak of the melting endotherm, while the Tg was taken as the mid point of heat capacity change respectively.

Thermogravemetric Analysis (TGA).

To determine the thermal stability and decomposition profile of the samples, TGA was carried out on a Perkin Elmer Pyris 1 thermogravemetric analyser calibrated using Nickel and Iron standards. Each sample was weighed to c.a. 7 mg and placed in a platinum pan and heated from 30° C. to 700° C. at the heating rate of 10° C./min under an air atmosphere.

Dynamic Mechanical Analysis (DMA).

DMA was carried out on a Perkin-Elmer Mechanical Analyzer. Dynamic measurements were made in extension mode on clamped film samples with dimensions of 5×2.8×0.5 mm. The experiments were performed under nitrogen atmosphere at a temperature range of −100° C. to 50° C. at a heating rate of 2° C./min and frequency of 0.1, 1 and 10 Hz. The Tg was identified by the sharp drop in storage modulus and the corresponding peak in the loss modulus. DMA glass transition temperature is frequency dependent and detectable at higher temperature compared to the quasistatic DSC data. The temperature at the maximum point of the loss modulus (E") was taken as the measure of the glass transition temperature.

Gel Permeation Chromatography.

Molecular weight distribution were obtained by gel permeation chromatography (GPC) using PL gel 5 mm mixed-C +PL gel column (Perkin Elmer) with PELV 290 UV-Vis detector set at 254 nm Spectroscopic grade chloroform was used as the eluent at flow rate of 1.0 ml/min. Sample concentration of 1 wt % and injection volumes of 500 μl. A molecular weight calibration curve was generated with polystyrene standards with low polydispersity using the Turbochrom 4.0 software.

X-Ray Diffraction (XRD) Analysis.

XRD was performed at room temperature and diffraction patterns were collected on a Siemens D500 diffractometer fitted with a Cu—Kα radiation source. The x-ray beam was C$\mu$-Kα ($\lambda$=0.1514 nm) radiation operated, at 40 KV and 30 mA. Data was obtained from 2-60° C. (2θ) at a scanning speed of 0.1° C./min.

16S rDNA Identification.

The three strains out of the 32 soil isolates capable of accumulating PHA with TA as the sole carbon and energy source were selected and classified by sequence analysis of 16S rRNA genes. Each isolate was grown on LB agar. The genomic DNA of each bacterium was extracted as follows. Strains were cultured in 30 ml of LB medium for 24 h with shaking, 200 rpm at 30° C. Cells were harvested by centrifugation at 4000×g for 10 min, washed twice in 10% sucrose solution and resuspended in 10 ml of lysis solution (0.3M sucrose, 25 mM EDTA, 25 mM Tris-HCl, pH 7.5 containing 2 U of RNase). Lysozyme (Sigma, 10 mg) was added and the bacterial suspension incubated at 37° C. for 20 min. 10% SDS (1 ml) and proteinase K (Sigma, 5 mg) were added with further incubation at 55° C. for 1 h. After addition of 5M NaCl (3.6 ml) and chloroform 15 ml, the sample was rotated end-over-end for 20 min. After centrifugation at 6000×g for 20 min, the aqueous phase was transferred with wide bore pipette into clean tube. The DNA was precipitated by addition of 1 volume of isopropanol and spooled using a sealed Pasteur pipette before being transferred into a micro-centrifuge tube and rinsed with 1 ml of 70% ethanol. Air dried DNA was dissolved in TE buffer (10 mM Tris-HCl, pH 7.4 and 10 mM EDTA). The 16S rRNA genes were amplified by PCR using primers 27F (agagtttgatcmtggctcag) presented as SEQ ID NO. 4, and 1392R (acgggcggtgtgtgtrc) presented as SEQ ID NO. 5, and the sequences were determined by GATC-Biotech, Germany. The resulting 16S rDNA sequences were compared to known sequences in the NCBI GenBank database by BLAST programme. The resulting sequences, presented as SEQ ID NOs 1-3 are discussed below with reference to Table 2.

RESULTS

Polyethylene Terephthalate Pyrolysis.

The pyrolysis of PET resulted in the generation of a solid, liquid and gaseous fraction, as shown in Table 1 below.

TABLE 1

| Product Composition | Weight percentage (%) |
|---|---|
| SOLIDS | 77 |
| Terephthalic acid | 51.0 |
| Oligomers | 20.0 |
| Benzoic acid | 1.0 |
| others | 5.0 |
| OIL | 6.3 |
| Ethylene glycol | 0.75 |
| Acetic aldehyde | 5.10 |
| Others | 0.45 |
| GASES | 18 |
| CO$_2$ | 13.0 |
| CO | 3.5 |
| Hydrogen | 0.18 |
| Ethene | 1.0 |
| Others | 0.34 |

66% of the solid fraction was in the form of monomeric TA, and almost 26% of the solid fraction was made up of oligomers of TA. The whole solid fraction was desublimated as described above to create a white powder, collected and used as a feedstock for PHA synthesis using the bacterial strains of the invention. The addition of the solid fraction of PET pyrolysis (in the form of the white powder) to an equimolar solution of sodium hydroxide resulted in the hydrolysis of the oligomers and increase in the proportion of TA making up the solid fraction. The solid fraction dissolved in sodium hydroxide contained 99% TA monomer in the form of sodium terephthalate. The pyrolysis liquid (oil) fraction made up 6.3% of the total weight of the pyrolysis products and contained predominantly acetic aldehyde and minor amounts of ethylene glycol. The gaseous fraction made up 18% of the pyrolysis products and contained predominantly CO$_2$. The liquid and gaseous fraction were burned to provide energy for the pyrolysis of PET.

As described above, of the 32 isolates screened only three accumulated detectable levels of PHA. These three organisms were identified using 16S rDNA techniques as described above. All three strains shared 99% homology with known *Pseudomonas* species (Table 2). Two of the three *Pseudomonas* strains GO16 and GO19 were found to be from the species *putida*, and are presented as SEQ ID NOs 1 and 2 respectively. The other strain *Pseudomonas* GO23 was found to be from the species *frederiksbergensis*, and is presented as SEQ ID NO 3.

TABLE 2

| Isolate PHA accumulators | Closest match from GenBank: Accession number | Classification | % Homology | % Coverage |
|---|---|---|---|---|
| GO16 (SEQ ID NO. 1) | DQ133506 | *Pseudomonas putida* | 99 | 97 |
| GO19 (SEQ ID NO. 2) | AY512611 | *Pseudomonas putida* | 99 | 99 |
| GO23 (SEQ ID NO. 3) | AJ249382 | *Pseudomonas frederiksbergensis* | 99 | 99 |

PHA Composition

Figure 2:
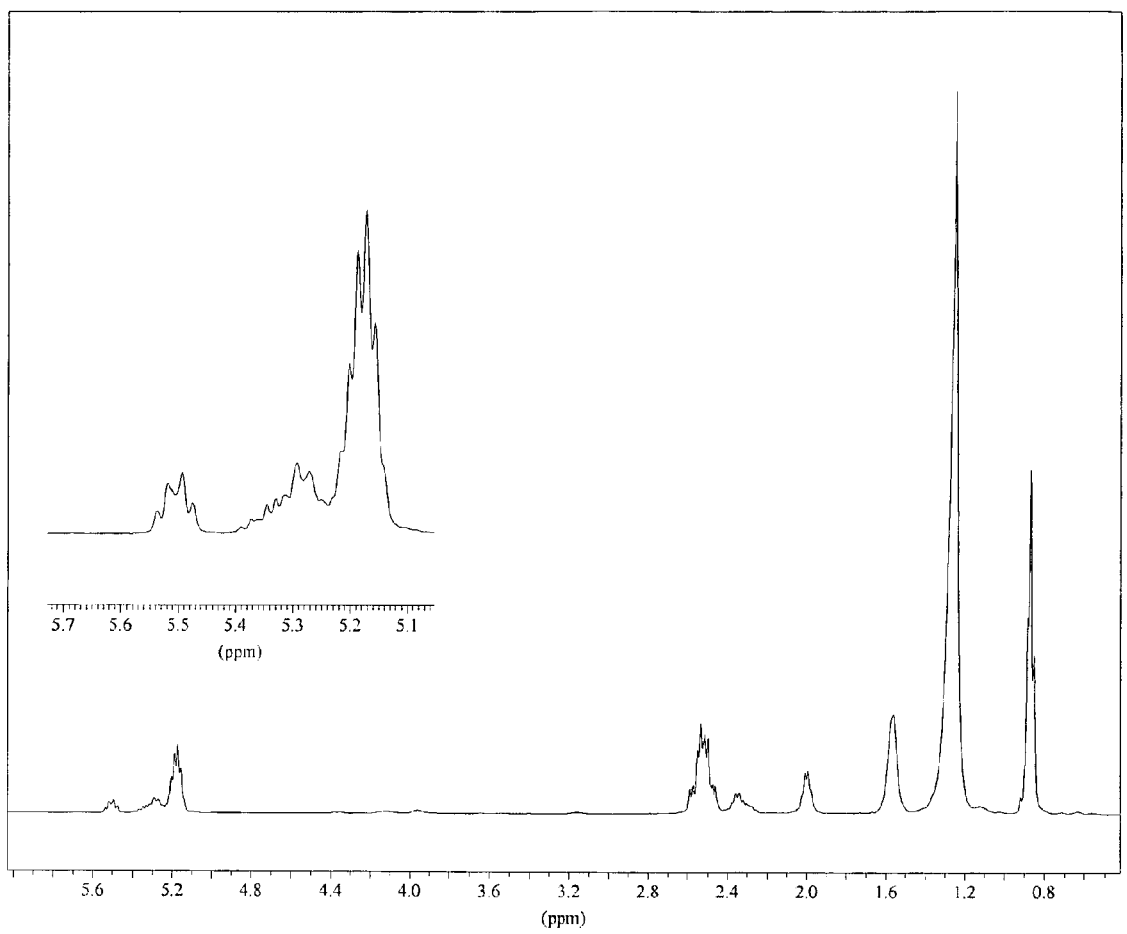
FIG. 2. 400 MHz $^1$HNMR spectrum of the mclPHA isolated from *P. putida* GO19 recorded at 20° C. in CDCl$_3$.
Figure 3:
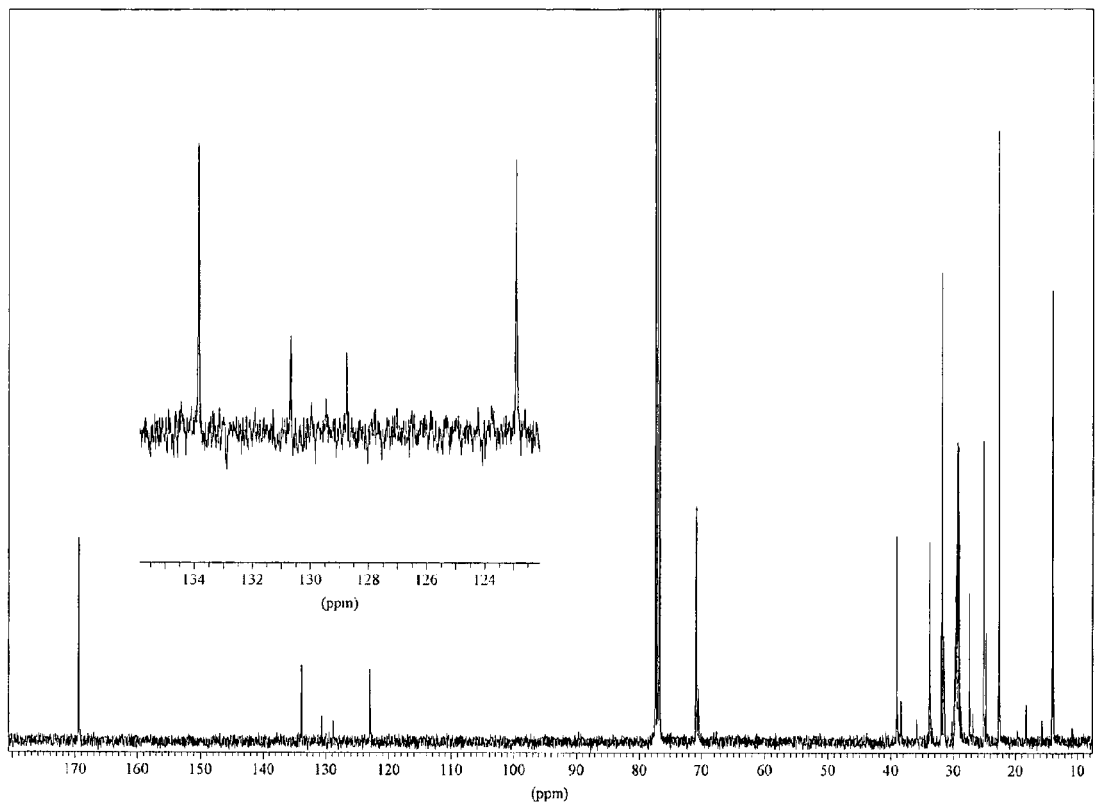
FIG. 3. $^{13}$C NMR spectrum of the mclPHA isolated from *P. putida* GO19 recorded at 20° C. in CDCl$_3$.

The $^1$H-NMR and $^{13}$C spectra for the PHA produced from the strain GO19 are shown in FIGS. 2 and 3 respectively. Peak assignments were typical of medium chain length PHA derivates.

Conversion of PET Derived Sodium Terephthalate to PHA in Shake Flask Experiments.

All three strains according to the invention accumulated PHA to between 23 and 27% of the total cell dry weight achieved, when supplied with either commercially available TA (sodium salt) or TA (sodium salt) derived from the pyrolysis of PET. Each of the strains GO16, GO19 and GO23 produced high quality PHA, namely mclPHA. Specifically, the PHA accumulated included 3-hydroxyalkanoic acid monomers containing 8, 10 and 12 carbons (Table 3). The commercially available TA (sodium salt) was used as a comparison to PET derived TA. PHA levels and composition were identical from both sources.

TABLE 3

| Bacterial strain | PHA(% CDW) | 3-OH-OCT* | 3-OH-DEC** | 3-OH-DODEC*** |
|---|---|---|---|---|
| P. Putida GO16 | 27 | 22 | 48 | 30 |
| P. putida GO19 | 23 | 24 | 45 | 31 |
| P. frederiksbergensis GO23 | 24 | 19 | 44 | 37 |

*3-OH-OCT = 3-hydroxyoctanoic acid,
**3-OH-DEC = 3-hydroxydecanoic acid,
***3-OH-DODEC = 3-hydroxydodecanoic acid.

While the sequence homology of 16S rDNA indicated a strong similarity between these bacteria, often closely related species have differing PHA accumulation abilities. Indeed the PHA composition of all three strains looks almost identical (Table 3). However, PHA from *P. putida* GO23 contained a higher proportion of 3-hydroxydodecanoic acid (12 carbons) compared to PHA from the other two strains.

Figure 1:
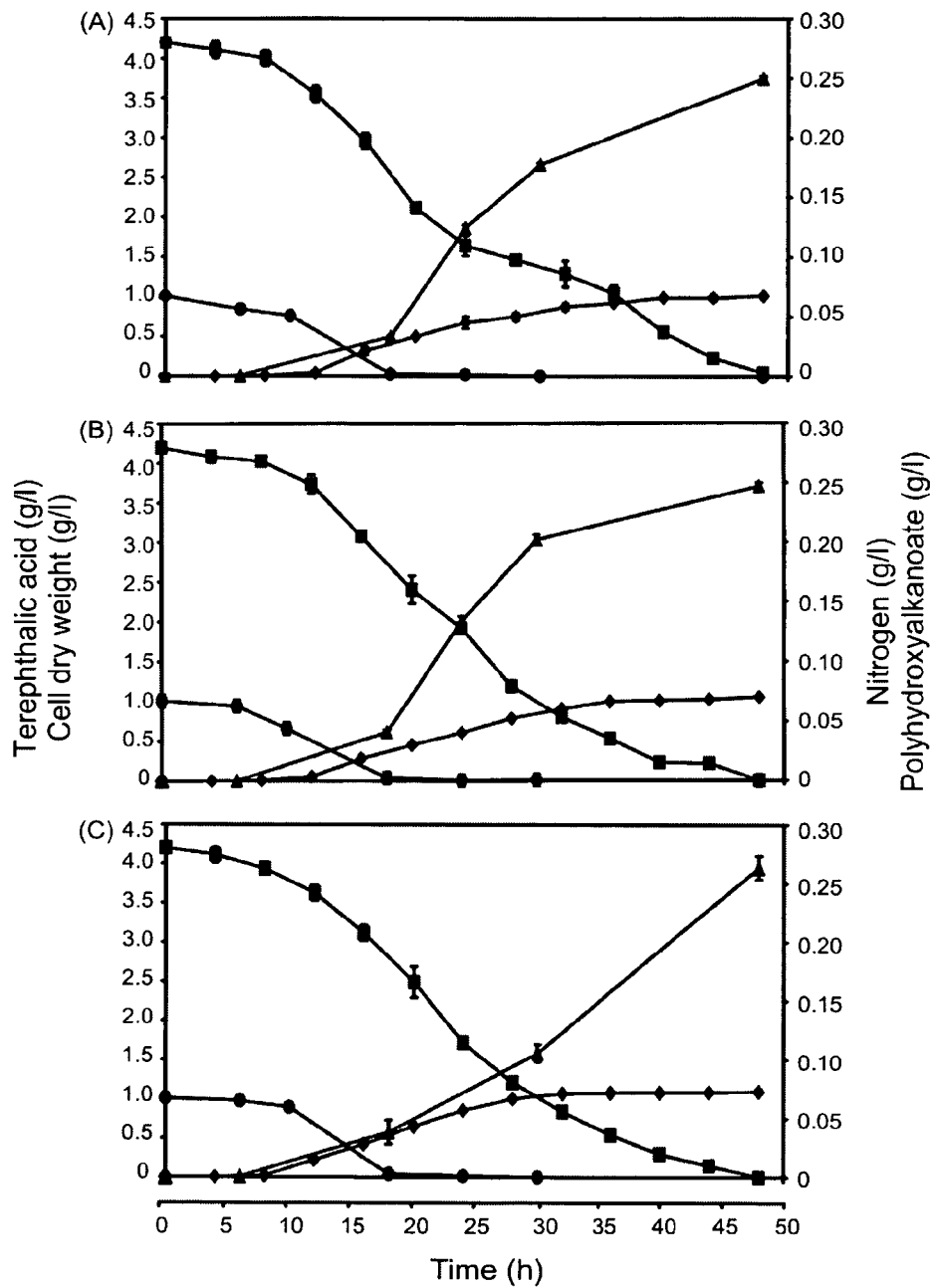
FIG. 1. PHA accumulation by (A) *Pseudomonas putida* GO16, (B) *Pseudomonas putida* GO19 and (C) *Pseudomonas frederiksbergensis* GO23 in shake flask containing growth medium consisting of 4.2 of sodium terephthalate and 67 mg/l of nitrogen at 30° C. CDW g/l (■), PHA accumulation g/l (▲), TA concentration (♦) and nitrogen concentration g/l (●) supplied as sodium ammonium phosphate were all monitored over a 48 h period. All data shown is the average of at least three independent determinations.

PHA accumulation by each of the three strains was monitored over time to determine when the onset of PHA occurred as well as the time course for PHA production. All three organisms were grown in shake flasks under the nitrogen limited conditions with 4.2 g/l of sodium terephthalate (generated by PET pyrolysis). Nitrogen concentration (as ammonium), TA concentration, cell dry weight and quantity of PHA accumulated were monitored (see FIG. 1). All three bacteria had similar growth patterns, they showed a long lag period in growth (of between 8-12 h) which coincided with a lag in TA utilization, despite being grown in precultures overnight on TA (4.2 g/l). During the exponential phase of growth strains GO16, GO19 and GO23 consumed TA at 0.135 g/l/h, 0.157 g/l/h and 0.121 g/l/h respectively and had specific growth rates of 0.04 $h^{-1}$, 0.043 $h^{-1}$, and 0.049 $h^{-1}$. All three strains consumed TA fully within the same period of time (FIG. 1).

PHA Material Properties

The properties of PHA polymer extracted from GO16, GO19 and GO23 are shown in Table 4.

Gel permeation chromatography (GPC) analysis showed the PHA polymers ranged in molecular weight (Mw) from 74 kDa to 123 kDa (Table 4). The molecular weight distribution (Mw/Mn) of the PHAs ranged from 1.9 to 2.4 (Table 4) and these values are typical for mclPHAs. The DSC analysis showed that PHA polymers produced by the method of the invention are partially crystalline, as evidenced by the presence of a melting peak. All three polymers produced with the different bacterial strains of the invention showed similar Tg, with slight changes in their Tm and ΔHm values (Table 4). X-ray diffraction (XRD) of cast films was used to calculate the crystallinity of the polymers. The strong diffraction peaks were located at the $2\theta=19.58$, 21.38 and 19.38 for PHA samples produced from GO16, GO19 and GO23 respectively. The calculated crystallinity values for GO16, GO19 and GO23 are shown in Table 4. All three PHA products had similar thermal degradation patterns. Peak degradation maximum occurred at approximately 308° C. with a high temperature shoulder most evident at approximately 350° C. in the differential thermograph. Polymer degradation was completed by 370° C. with all residual carbonaceous materials produced during thermal degradation being burnt at about 600° C. Thus, the PHAs produced by all three strains were thermoplastics.

Example 1 (B)

Out of the original 32 isolates described in Example 1 (A) above, six of the remaining 29 isolates which were found not to produce PHA were selected at random and classified by sequence analysis of 16S rRNA genes in accordance with the procedure as described in Example 1 (A). The resulting 16S rDNA sequences were compared to known sequences in the NCBI GenBank database by BLAST programme, and the results are shown in Table 5.

TABLE 5

| Isolate (PHA non producers) | Closest match from GenBank: Accession number | Classification | % Homology | % Coverage |
|---|---|---|---|---|
| GO 13A (SEQ ID NO. 6) | AB008001 | *Pseudomonas putida* | 99 | 99 |
| GO 1 (SEQ ID NO. 7) | EU111737.2 | *Pseudomonas putida* | 100 | 99 |
| GO 6 (SEQ ID NO. 8) | AY823622.1 | *Pseudomonas putida* | 100 | 99 |
| GO 8 (SEQ ID NO. 9) | EF093130.1 | *Pseudomonas* sp. | 99 | 99 |

TABLE 4

| Strain | Melting point enthalpy ΔHm | Crystalline melting temperature Tm (° C.) | Glass transition temperature Tg(° C.) | Molecular weight MW | Number-average molecular weight MN | Polydispersity index PD | % Crystallinity |
|---|---|---|---|---|---|---|---|
| GO 16 | 12.75 | 35.36 | −53.13 | 7.43 × $10^4$ | 3.76 × $10^4$ | 1.97 | 26.8 |
| GO 19 | 10.75 | 34.19 | −53.14 | 12.32 × $10^4$ | 5.19 × $10^4$ | 2.37 | 18.71 |
| GO 23 | 11.78 | 35.75 | −53.38 | 9.38 × $10^4$ | 4.4 × $10^4$ | 2.10 | 31.09 |

TABLE 5-continued

| Isolate (PHA non producers) | Closest match from GenBank: Accession number | Classification | % Homology | % Coverage |
|---|---|---|---|---|
| GO 14 (SEQ ID NO. 10) | Y17052 | *Burkholderia glathei* | 99 | 99 |
| TA 1 (SEQ ID NO 11) | AM402950 | *Stenotrophomonas sp.* | 98 | 99 |

Four of the six isolates were found to be from the genus *Pseudomonas*, with three of the four *Pseudomonas* strains being specifically from the species *putida*. The utilization of terephthalic acid (sodium salt) by these six strains was monitored as described in Example 1 (A), and it was found that although sodium terephthalate was utilized, no PHA was produced. Since it has been shown that some strains of *Pseudomonas putida* (e.g. the strains shown in Table 5) are incapable of accumulating PHA from sodium terephthalate, (presumably simply producing biomass instead), it is surprising that *Pseudomonas putida* strain GO16 and *Pseudomonas putida* strain GO19 were found to accumulate PHA from sodium terephthalate. Similarly, in view of the fact that a *Pseudomonas sp.* strain was incapable of accumulating PHA from sodium terephthalate, it is also surprising that *Pseudomonas frederiksbergensis* strain GO23 was found to accumulate PHA from sodium terephthalate.

Example 2

Comparative Example

Three conventional bacterial strains known to utilize TA as a sole source of carbon and energy, namely *Comamonas testosteroni* YZW-D, *Comamonas testosteroni* T-2 and *Comamonas testosteroni* PSB-4, identified in Table 6, were tested for PHA accumulation. These three strains are known to utilize TA, but did not produce any PHA (presumably simply producing biomass instead). The utilization of terephthalic acid (sodium salt) was monitored as described in Example 1 (A), and it was found that although sodium terephthalate was utilized, no PHA was produced.

TABLE 6

| Source | Strain |
|---|---|
| Wang et al[1] | *Comamonas testosteroni* YZW-D |
| DSMZ[2] | *Comamonas testosteroni* T-2 |
| DSMZ[2] | *Comamonas testosteroni* PSB-4 |

[1]Wang Y. Z.; Zhou Y.; Zylstra G. J. Molecular analysis of isophthalate and terephthalate degradation by *Comamonas testosteroni* YZW-D, *Environ Health Perspect*, 1995. 103 Suppl 5:9-12.
[2]DSMZ = the German resource centre for biological material. Junker F.; Salter E.; Schlafli Oppenberg H. R.; Kroneck P. M.; Leisinger T.; Cook A. Degradative pathways for p-toluenecarboxylate and p-toluenesulfonate and their multicomponent oxygenases in *Comamonas testosteroni* strains PSB-4 and T-2. *Microbiology*. 1996. 142, 2419-2427.

This comparative example is further evidence of the surprising result achieved by the strains of the invention, *Pseudomonas putida* strain GO16, *Pseudomonas putida* strain GO19 and *Pseudomonas frederiksbergensis* strain GO23. Given that known TA degraders were found to be incapable of producing PHA, it is surprising that the strains of the invention were capable of accumulating PHA from TA (sodium salt).

In summary, although some strains exist which are capable of degrading TA, and some strains exist which are capable of producing PHA, no strains have existed until now which are capable of utilizing TA to produce PHA.

The invention claimed is:

1. A method for producing polyhydroxyalkanoate (PHA), comprising (i) culturing in a culture medium comprising terephthalic acid and/or a salt thereof and/or an ester thereof a bacterial strain which is capable of accumulating PHA from terephthalic acid or a salt or ester thereof and which is *Pseudomonas putida* strain GO16 having the accession number NCIMB 41538; and (ii) recovering the PHA produced from the culture medium.

2. The method as claimed in claim 1, wherein the PHA recovered from the culture medium comprises at least 80% medium chain length (mcl) PHA.

3. The method as claimed in claim 2, wherein at least 80% of the mclPHA comprises repeating units of C8, C10 and C12 monomers.

4. The method as claimed in claim 3, wherein the mclPHA comprises repeating units of C8, C10 and C12 monomers in a respective amount by weight of mclPHA of 15%-25% C8, 40%-50% C10 and 30%-40% C12.

5. The method as claimed in claim 1, wherein a salt of terephthalic acid is present in the culture medium, and wherein, the salt is selected from the group consisting of alkali metal and alkaline earth metal salts and mixtures thereof, especially sodium and potassium salts, and magnesium, calcium and barium salts.

6. The method as claimed in claim 5, wherein the salt is a mono- or di-sodium or potassium salt of terephthalic acid.

7. The method as claimed in claim 6, wherein the salt is monosodium terephthalate.

8. The method as claimed in claim 1, wherein an ester of terephthalic acid is present in the culture medium, and wherein, the ester is selected from the group consisting of mono- and di-esters of terephthalic acid and mixtures thereof, especially mono- and di-C1-C4 alkyl esters and mono- and di-glycol esters.

9. The method as claimed in claim 1, wherein the terephthalic acid or salt or ester thereof may be obtained from hydrolysis or pyrolysis of polyethylene terephthalate (PET).

10. The method as claimed in claim 1, wherein the method comprises culturing the one or more strains in the culture medium for a period of from about 12 hours to about 72 hours, at a temperature of from about 25° C. to about 35° C.

11. The method as claimed in claim 1, wherein the culture medium is nitrogen limited, with a maximum nitrogen content of about 0.067-0.5 g/l culture medium.

12. The method as claimed in claim 1, wherein the PHA recovered from the culture medium comprises at least 85% medium chain length (mcl) PHA.

13. The method as claimed in claim 1, wherein the PHA recovered from the culture medium comprises at least 90% medium chain length (mcl) PHA.

14. The method as claimed in claim 1, wherein the PHA recovered from the culture medium comprises at least 95% medium chain length (mcl) PHA.

15. The method as claimed in claim 2, wherein at least 85% of the mclPHA comprises repeating units of C8, C10 and C12 monomers.

16. The method as claimed in claim 2, wherein at least 90% of the mclPHA comprises repeating units of C8, C10 and C12 monomers.

17. The method as claimed in claim 2, wherein at least 95% of the mclPHA comprises repeating units of C8, C10 and C12 monomers.

* * * * *